United States Patent
Mezghani et al.

(10) Patent No.: US 12,013,511 B2
(45) Date of Patent: Jun. 18, 2024

(54) GEOLOGICAL CORE LABORATORY SYSTEMS AND METHODS

(71) Applicant: Saudi Arabian Oil Company, Dhahran (SA)

(72) Inventors: Mokhles M. Mezghani, Dhahran (SA); Bodong Li, Dhahran (SA); Abdul Hafiz Masri, Dhahran Hills (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 18/315,252

(22) Filed: May 10, 2023

(65) Prior Publication Data
US 2023/0280491 A1    Sep. 7, 2023

Related U.S. Application Data

(62) Division of application No. 16/793,494, filed on Feb. 18, 2020, now Pat. No. 11,686,876.

(51) Int. Cl.
*G01V 3/34*    (2006.01)
*G01N 33/24*   (2006.01)
(Continued)

(52) U.S. Cl.
CPC .............. *G01V 3/34* (2013.01); *G01V 3/38* (2013.01); *G01N 33/241* (2013.01); *G01V 3/08* (2013.01)

(58) Field of Classification Search
CPC ... G01V 3/34; G01V 3/38; G01V 3/08; G01N 33/241
See application file for complete search history.

(56) References Cited

U.S. PATENT DOCUMENTS 7,054,753 B1    5/2006  Williams et al.
8,849,679 B2    9/2014  Wang et al.
(Continued)

FOREIGN PATENT DOCUMENTS

JP    2002296189 A    10/2002

OTHER PUBLICATIONS

Engadget "iPanel von Creston perfektioniert iPad für Home Automation" available as of Mar. 6, 2019 at: https://www.engadget.com/de/2010/09/17/ipanel-von-creston-perfektioniert-ipad-fur-home-automation/; pp. 1-7.
(Continued)

*Primary Examiner* — Mohamed Charioui
*Assistant Examiner* — Lynda Dinh
(74) *Attorney, Agent, or Firm* — Bracewell LLP; Constance G. Rhebergen; Brian H. Tompkins

(57) ABSTRACT

A geological core inspection system that includes a table to support core samples for inspection, a robotic geological core inspection system including a core sample sensing system to acquire sample inspection data (including an imaging sensor and a core sample position sensor), a core sample interaction system (including a dispensing system and a scoring system), and a robotic positioning system, and a control and communications system to provide for remote control of the core sample sensing system. The system further including a remote geological core inspection system to receive and communicate remote commands specifying requested operations of the robotic geological core inspection system (the control and communications system adapted to control operation of the core sample sensing system in response to the remote commands to perform the requested operations) and receive and present core data.

10 Claims, 4 Drawing Sheets

(51) Int. Cl.
*G01V 3/08* (2006.01)
*G01V 3/38* (2006.01)

(56) References Cited

U.S. PATENT DOCUMENTS

| | | | |
|---|---|---|---|
| 9,196,058 | B2 | 11/2015 | Mezghani |
| 9,507,047 | B1 | 11/2016 | Dvorkin et al. |
| 9,612,231 | B2 | 4/2017 | Pottorf et al. |
| 9,796,089 | B2 | 10/2017 | Lawrence, III et al. |
| 2003/0112152 | A1 | 6/2003 | Pickett |
| 2009/0195655 | A1 | 8/2009 | Pandey |
| 2013/0041508 | A1 | 2/2013 | Hu et al. |
| 2016/0194940 | A1 | 7/2016 | Andersen et al. |
| 2016/0306074 | A1 | 10/2016 | Andersen et al. |
| 2017/0004650 | A1* | 1/2017 | Caliskan ............... G06T 7/00 |
| 2017/0286802 | A1 | 10/2017 | Mezghani et al. |
| 2017/0362908 | A1* | 12/2017 | Sale .................. E21B 25/08 |
| 2018/0018817 | A1 | 1/2018 | Caliskan et al. |
| 2018/0188225 | A1 | 7/2018 | Viscarra Rossel et al. |
| 2018/0347354 | A1 | 12/2018 | Li et al. |
| 2019/0040735 | A1* | 2/2019 | McLeod ............... E21B 25/16 |
| 2019/0351804 | A1 | 11/2019 | Kanck et al. |

OTHER PUBLICATIONS

Enplug Blog "The Complete Meeting and Signage Guide" available as of Mar. 6, 2019 at: https://blog.enplug.com/meeting-conference-room-signage-guide; pp. 1-7.

Hahn Automation Plastics "ProLine PL1000 3-Axis Robot" available as of Mar. 6, 2019 at: https://www.hahnautomationplastics.com/proline-pl1000-3-axis-robots; pp. 1-3.

Inspect-online; "Lumenera's High Resolution 29 Megapixel Large Format USB 3.0 Camera" Jun. 30, 2017, available as of Feb. 18, 2020 at: https://www.inspect-online.com/en/products/vision/lumeneras-high-resolution-29-megapixel-large-format-usb-30-camera; 2 pgs.

International Search Report and Written Opinion for International Application No. PCT/US2021/018591 (SA51164), report mail date Jul. 12, 2021; pp. 1-17.

Nordson Sealent Equipment "033 1-Part Snuf-Bak Series" available as of Mar. 6, 2019 at: https://www.nordson.com/en/divisions/sealant-equipment/products/valves/033-1-part-snuf-bak-series; p. 1.

* cited by examiner

GEOLOGICAL CORE LABORATORY SYSTEMS AND METHODS

CROSS-REFERENCE TO RELATED APPLICATIONS

This application is a divisional of and claims priority from U.S. Non-provisional application Ser. No. 16/793,494 filed Feb. 18, 2020, and titled "GEOLOGICAL CORE LABORATORY SYSTEMS AND METHODS," a copy of which is incorporated by reference in its entirety for purposes of United States patent practice.

FIELD

Embodiments relate generally to geological core inspection, and more particularly to remote geological core inspection.

BACKGROUND

A well generally includes a wellbore (or "borehole") that is drilled into the earth to provide access to a geologic formation below the earth's surface (or "subsurface formation"). A well may facilitate the extraction of natural resources, such as hydrocarbons and water, from a subsurface formation, facilitate the injection of substances into the subsurface formation, or facilitate the evaluation and monitoring of the subsurface formation. In the petroleum industry, hydrocarbon wells are often drilled to extract (or "produce") hydrocarbons, such as oil and gas, from subsurface formations.

Developing a hydrocarbon well for production typically involves several stages, including a drilling stage, a completion stage and a production stage. The drilling stage typically involves drilling a wellbore into a portion of the formation that is expected to contain hydrocarbons (often referred to as "hydrocarbon reservoir" or "reservoir"). The drilling process typically employs a drilling rig that sits at the earth's surface and facilitates a variety of operations, such as operating a drill bit to drill the wellbore. The completion stage involves operations for making the well ready to produce hydrocarbons, such as installing casing, perforating the casing, installing production tubing, installing downhole valves for regulating production flow, or pumping fluids into the well to fracture, clean or otherwise prepare the reservoir and well to produce hydrocarbons. The production stage normally involves producing hydrocarbons from the reservoir by way of the well. During the production stage, the drilling rig is typically replaced with valves that are operable to regulate pressure in the wellbore, control production flow from the wellbore, or provide access to the wellbore. An outlet valve is often connected to a distribution network of midstream facilities, such as tanks, pipelines or transport vehicles that transport the production to downstream facilities, such as refineries or export terminals.

The various stages of developing a hydrocarbon well normally include challenges that are addressed to successfully develop the well. For example, in an effort to accurately characterize a well, a well operator may conduct coring operations to extract and collect core samples from the well (e.g., cylindrically shaped samples of formation rock), and the core samples may be assessed to identify characteristics of the well (and the surrounding formation) at corresponding depths. The characteristics may be assembled to generate core logs or other information that characterize the well and the surrounding formation at different depths.

SUMMARY

Collection and assessment of samples of formation rock (or "core samples" or "cores") can be an important aspect of successfully and efficiently developing a hydrocarbon well. For example, core samples may enable geoscientists to directly assess properties of the formation rock, such as density, porosity, permeability, wettability, organic matter content, fluid content, or the like, in a laboratory environment. This information can be used, for example, to calibrate well log data obtained by way of well logging operations, to generate geological models of the subsurface formation, or to determine well location, well drilling or well operating parameters.

Core samples are typically collected by way of a coring operation and are transported to a laboratory facility for assessment. For example, during a drilling of a wellbore into a subsurface formation, one more coring operations may be conducted to cut and extract cores (e.g., cylindrical continuous section of rock) from different depths in the formation. The core samples may be transported to a laboratory where they are physically assessed to determine characteristics (e.g., density, porosity, permeability, fluid saturation, lithology or texture) of the core samples and the formation. The laboratory assessment typically involves having one or more geologists physically present in the laboratory to conduct "on-site" inspection and testing of the core samples in the laboratory environment. This can include, for example, using dedicated tools, such as a microscope to investigate the rock properties or a camera to acquire photos of the core samples. Unfortunately, the laboratory can become physically crowded with core samples, personnel and equipment, making it difficult to efficiently and fully assess the core samples. Further, geologists that are not able to visit the laboratory in person may have to rely on the results of prior on-site inspections for subsequent assessment of the core samples and the formation. These factors can make it difficult for geologists to verify information or to make complete assessments in a traditional core laboratory environment.

In view of deficiencies of existing geological core laboratory systems and assessment techniques, provided are embodiments of a robotic geologic core inspection system. The described embodiments may enable real-time, remote controlled, collaborative and interactive assessment of core samples located in a core laboratory environment. In some embodiments, a robotic geological core inspection system includes the following: (1) a robotic positioning system; (2) a core sample sensing system; (3) a core sample interaction system; and (4) a control/communications system.

Provided in some embodiments is a geological core inspection system that includes the following: a geological core inspection table adapted to physically support core samples for inspection in a geological core inspection laboratory; a robotic geological core inspection system including: a core sample sensing system adapted to acquire core sample inspection data that is indicative of characteristics of the core samples, the core sample sensing system including: a core sample imaging sensor adapted to acquire images of the core samples; and a core sample position sensor adapted to sense a position of the robotic geological core inspection system relative to the core samples; a core sample interaction system including: a dispensing system adapted to apply substances to the core samples; and a scoring system adapted to physically score the core samples; and a robotic positioning system disposed above the geological core inspection table and adapted to provide for positioning of the core sample sensing system and the core sample interaction system relative to the core samples; and a control and communications system adapted to provide for remote control of the core sample sensing system, the core sample interaction system, and the robotic positioning system; and a remote geological core inspection system adapted to be located physically remote from the geological core inspection laboratory, the remote geological core inspection system adapted to: receive remote commands specifying requested operations of the robotic geological core inspection system; communicate, to the control and communications system, the remote commands, the control and communications system adapted to, in response to receiving the remote commands, control operation of the core sample sensing system, the core sample interaction system, and the robotic positioning system to perform the requested operations; and receive, from the control and communications system, core data; and present, in response to receiving the core data, the core data.

In some embodiments, the dispensing system includes a spray system adapted to spray substances on surfaces of the core samples. In some embodiments, the scoring system includes a scoring arm adapted to physically score surfaces of the core samples. In some embodiments, the core sample imaging sensor is adapted to acquire images of the operation of the core sample interaction system, and where the core data includes the images of the operation of the core sample interaction system. In some embodiments, the control and communications system is adapted to, in response to receiving a remote command requesting a scoring operation for a given core sample: operate the core sample interaction system and the robotic positioning system to conduct a scoring of the given core sample; operate the core sample imaging sensor to acquire an image of the scoring of the given core sample; and send, to remote geological core inspection system, core data including the image of the scoring of the given core sample, where the remote geological core inspection system is adapted to display the image of the scoring of the given core sample. In some embodiments, the control and communications system is adapted to, in response to receiving a remote command requesting a spraying operation for a given core sample: operate the core sample dispensing system and the robotic positioning system to conduct a dispensing of a substance on the given core sample; operate the core sample imaging sensor to acquire an image of the dispensing of the substance on the given core sample; and send, to remote geological core inspection system, core data including the image of the dispensing of the substance on the given core sample, where the remote geological core inspection system is adapted to display the image of the dispensing of the substance on the given core sample. In some embodiments, the control and communications system is adapted to, in response to receiving a remote command requesting imaging of a given core sample: operate the robotic positioning system and the core sample imaging sensor to acquire an image of the given core sample; and send, to remote geological core inspection system, core data including the image of the given core sample, where the remote geological core inspection system is adapted to display the image of the given core sample.

Provided in some embodiments is a method of geological core inspection that includes the following: positioning, on a geological core inspection table in a geological core inspection laboratory, core samples for inspection, the geological core inspection laboratory including: a robotic geological core inspection system including: a core sample sensing system adapted to acquire core sample inspection data that is indicative of characteristics of the core samples, the core sample sensing system including: a core sample imaging sensor adapted to acquire images of the core samples; and a core sample position sensor adapted to sense a position of the robotic geological core inspection system relative to the core samples; a core sample interaction system including: a dispensing system adapted to apply substances to the core samples; and a scoring system adapted to physically score the core samples; and a robotic positioning system disposed above the geological core inspection table and adapted to provide for positioning of the core sample sensing system and the core sample interaction system relative to the core samples; and a control and communications system adapted to provide for remote control of the core sample sensing system, the core sample interaction system, and the robotic positioning system; receiving, by the control and communications system from a remote geological core inspection system located physically remote from the geological core inspection laboratory, a remote command specifying a requested operation of the robotic geological core inspection system; controlling, by the control and communications system in response to receiving the remote command, operation of the core sample sensing system, the core sample interaction system, and the robotic positioning system to perform the requested operation; and sending, by the control and communications system to the remote geological core inspection system, core data indicative of performance of the requested operation, where the remote geological core inspection system is adapted to present the core data.

In some embodiments, the dispensing system includes a spray system adapted to spray substances on surfaces of the core samples. In some embodiments, the scoring system includes a scoring arm adapted operable to physically score surfaces of the core samples. In some embodiments, performance of the requested operation includes the core sample imaging sensor acquiring images of the operation of the core sample interaction system, and where the core data includes the images of the operation of the core sample interaction system. In some embodiments, the method further includes the control and communications system, in response to the remote command requesting a scoring operation for a given core sample: operating the core sample interaction system and the robotic positioning system to conduct a scoring of the given core sample; operating the core sample imaging sensor to acquire an image of the scoring of the given core sample; and sending, to remote geological core inspection system, core data including the image of the scoring of the given core sample, where the remote geological core inspection system is adapted to display the image of the scoring of the given core sample.

In some embodiments, the method further includes the control and communications system, in response to the remote command requesting a spraying operation for a given core sample: operating the core sample dispensing system and the robotic positioning system to conduct a dispensing of a substance on the given core sample; operating the core sample imaging sensor to acquire an image of the dispensing of the substance on the given core sample; and sending, to remote geological core inspection system, core data including the image of the dispensing of the substance on the given core sample, where the remote geological core inspection system is adapted to display the image of the dispensing of the substance on the given core sample. In some embodiments, the method further includes the control and communications system, in response to the remote command requesting imaging of a given core sample: operating the robotic positioning system and the core sample imaging sensor to acquire an image of the given core sample; operating the core sample imaging sensor to acquire an image of the given core sample; and sending, to remote geological core inspection system, core data including the image of the given core sample, where the remote geological core inspection system is adapted to display the image of the given core sample.

Provided in some embodiments is a non-transitory computer readable storage medium including program instructions stored thereon that are executable by a computer processor to perform a geological core inspection including the following operations: positioning, on a geological core inspection table in a geological core inspection laboratory, core samples for inspection, the geological core inspection laboratory including: a robotic geological core inspection system including: a core sample sensing system adapted to acquire core sample inspection data that is indicative of characteristics of the core samples, the core sample sensing system including: a core sample imaging sensor adapted to acquire images of the core samples; and a core sample position sensor adapted to sense a position of the robotic geological core inspection system relative to the core samples; a core sample interaction system including: a dispensing system adapted to apply substances to the core samples; and a scoring system adapted to physically score the core samples; and a robotic positioning system disposed above the geological core inspection table and adapted to provide for positioning of the core sample sensing system and the core sample interaction system relative to the core samples; and a control and communications system adapted to provide for remote control of the core sample sensing system, the core sample interaction system, and the robotic positioning system; receiving, by the control and communications system from a remote geological core inspection system located physically remote from the geological core inspection laboratory, a remote command specifying a requested operation of the robotic geological core inspection system; controlling, by the control and communications system in response to receiving the remote command, operation of the core sample sensing system, the core sample interaction system, and the robotic positioning system to perform the requested operation; and sending, by the control and communications system to the remote geological core inspection system, core data indicative of the performance of the requested operation, where the remote geological core inspection system is adapted to present the core data.

Provided in some embodiments is a method of remote geological core inspection that includes the following: positioning, on a core sample inspection table, an array of core samples; conducting, by a robotic core inspection system, a scanning of the array of core samples to identify positions of the core samples of the array of core samples; generating, by the robotic core inspection system based on the positions of the core samples identified, a core sample mapping identifying locations of the core samples on the core sample inspection table; receiving, by the robotic core inspection system, a command to conduct an inspection operation for a given core sample of the core samples; determining, based on the core sample mapping, a location of the given core sample; positioning, by the robotic core inspection system, an inspection device proximate the location of the given core sample; and conducting, by the robotic core inspection system, the inspection operation for the given core sample.

In some embodiments, the scanning of the array of core samples includes capturing a photographic image of the array of core samples. In some embodiments, the scanning of the array of core samples includes capturing a physical profile of the core samples. In some embodiments, each core sample of the array of core samples includes a corresponding core identifier, and where the core sample mapping associates each core sample of the array of core samples with the corresponding core identifier. In some embodiments, the command to conduct an inspection operation for the given core sample identifies the core identifier corresponding to the given core sample, and where the location of the given core sample is determined based on a location of the core sample mapping that corresponds to the core identifier corresponding to the given core sample. In some embodiments, the inspection operation includes a sensing operation including moving a sensor proximate the location of the given core sample to sense a corresponding characteristic of the core sample. In some embodiments, the inspection operation includes an interactive operation including moving an interactive device proximate the location of the given core sample to physically interact with the core sample. In some embodiments, the inspection operation includes an interactive spraying operation including moving a spray device proximate the location of the given core sample and operating the spray system to spray a substance on a surface of the given core sample. In some embodiments, the inspection operation includes an interactive scoring operation including moving a scoring device proximate the location of the given core sample and operating the scoring system to score a surface of the given core sample.

Provided in some embodiments is a non-transitory computer readable storage medium including program instructions stored thereon that are executable by a computer processor to perform a geological core inspection including the following operations: conducting, by a robotic core inspection system, a scanning of an array of core samples positioned on a core sample inspection table in a geological core inspection laboratory to identify positions of the core samples of the array of core samples; generating, by the robotic core inspection system based on the positions of the core samples identified, a core sample mapping identifying locations of the core samples on the core sample inspection table; receiving, by the robotic core inspection system, a command to conduct an inspection operation for a given core sample of the core samples; determining, by the robotic core inspection system based on the core sample mapping, a location of the given core sample; positioning, by the robotic core inspection system, an inspection device proximate the location of the given core sample; and conducting, by the robotic core inspection system, the inspection operation for the given core sample.

Provided in some embodiments is a geological core inspection system that includes the following: a robotic core inspection system including a control and communications system a robotic core inspection system including non-transitory computer readable storage medium including program instructions stored thereon that are executable by a computer processor to perform a geological core inspection including the following operations: conducting a scanning of the array of core samples to identify positions of the core samples of the array of core samples; generating, on the positions of the core samples identified, a core sample mapping identifying locations of the core samples on the core sample inspection table; receiving a command to conduct an inspection operation for a given core sample of the core samples; determining, based on the core sample mapping, a location of the given core sample; positioning an inspection device proximate the location of the given core sample; and conducting the inspection operation for the given core sample.

Figure 1:
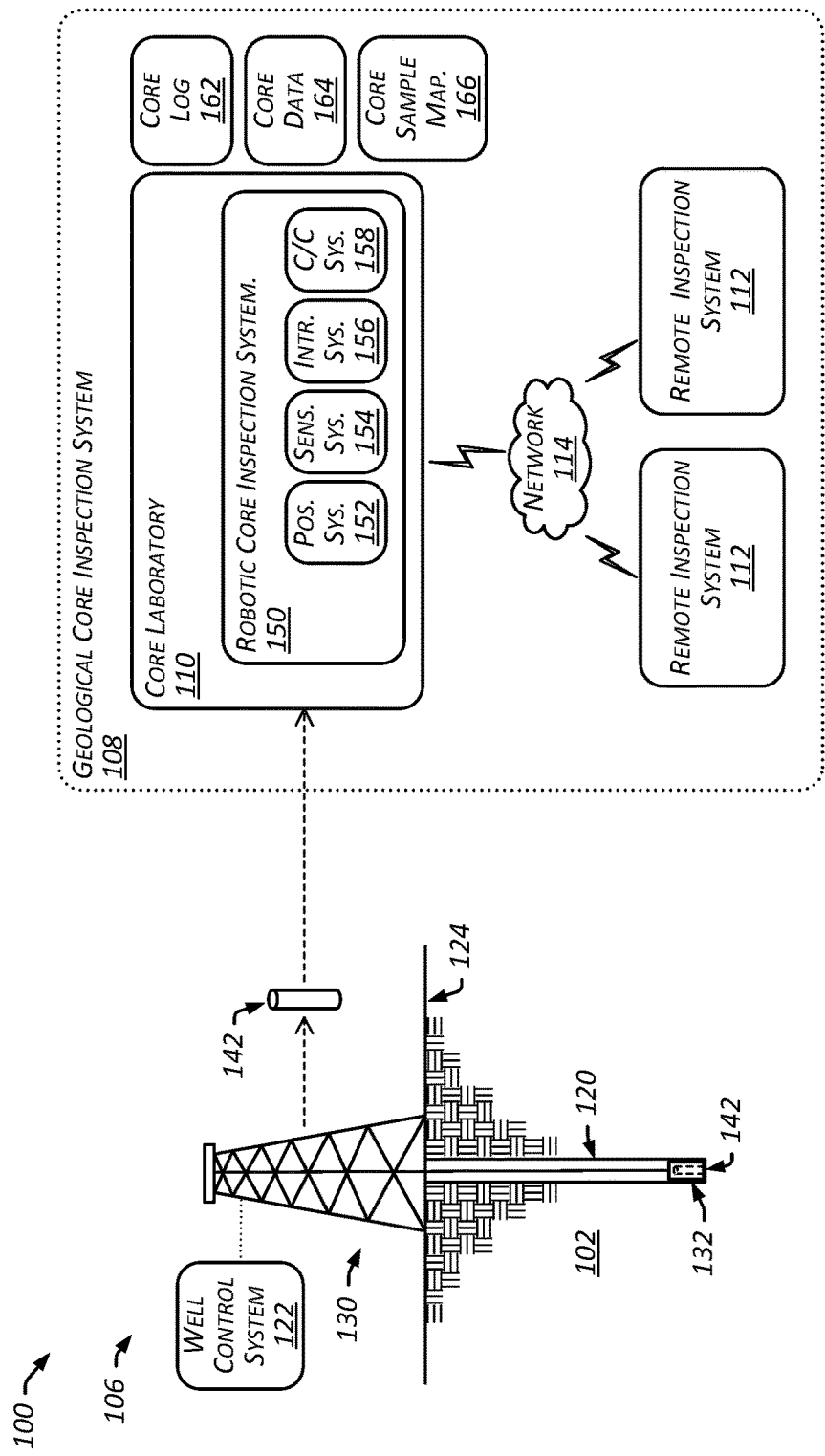
FIG. 1 is diagram that illustrates a geological core inspection environment in accordance with one or more embodiments.

While this disclosure is susceptible to various modifications and alternative forms, specific embodiments are shown by way of example in the drawings and will be described in detail. The drawings may not be to scale. It should be understood that the drawings and the detailed descriptions are not intended to limit the disclosure to the particular form disclosed, but are intended to disclose modifications, equivalents, and alternatives falling within the scope of the present disclosure as defined by the claims.

DETAILED DESCRIPTION

Described are embodiments of novel robotic geologic core inspection system systems and methods. The described embodiments may enable real-time, remote controlled, collaborative and interactive assessment of core samples located in a core laboratory environment. In some embodiments, a robotic geological core inspection system includes the following: (1) a robotic positioning system; (2) a core sample sensing system; (3) a core sample interaction system; and (4) a control/communications system.

FIG. 1 is a diagram that illustrates a geological core inspection environment 100 in accordance with one or more embodiments. In the illustrated embodiment, the geological core inspection environment 100 includes a subsurface formation ("formation") 102, a well system ("well") 106 and a geological core inspection system 108 that includes a geological core inspection laboratory ("core laboratory") 110 and one more remote geological core inspection systems ("remote inspection systems") 112 communicatively coupled by way of a network 114.

The formation 102 may include a porous or fractured rock formation that resides underground, beneath the Earth's surface (or "surface") 124. The formation 102 may include different layers of rock having varying characteristics, such as varying degrees of density, permeability, porosity, and fluid saturations. The formation 102 may include a hydrocarbon reservoir, and the well 106 may be a hydrocarbon well, such as an oil well, that extends into the reservoir. The reservoir may be defined by a portion of the formation 102 that contains (or that is at least determined to or expected to contain) a subsurface reservoir of hydrocarbons, such as oil and gas. In the case of the well 106 being operated as a production well, the well 106 may facilitate the extraction of hydrocarbons (or "production") from formation 102. In the case of the well 106 being operated as an injection well, the well 106 may facilitate the injection of substances, such as gas or water, into the formation 102. In the case of the well 106 being operated as a monitoring well, the well 106 may facilitate the monitoring of various characteristics of the formation 102, such as reservoir pressure or saturation.

The well 106 may include a wellbore 120, a well control system 122, and a drilling system 130. The well control system 122 may control various operations of the well 106, such as well drilling operations, well completion operations, well production operations, or well and formation monitoring operations. In some embodiments, the well control system 122 includes a computer system that is the same as or similar to that of computer system 1000 described with regard to at least FIG. 4.

The wellbore 120 (or "borehole") may include a drilled hole that extends from the earth's surface 124 into a target zone of the formation 102, such as a hydrocarbon reservoir. An upper end of the wellbore 120, at or near the surface 124, may be referred to as the "up-hole" end of the wellbore 120. A lower end of the wellbore 120, terminating in the formation 102, may be referred to as the "down-hole" end of the wellbore 120. The wellbore 120 may be created, for example, by a bit 132 of the drilling system 130 drilling through the formation 102. During a drilling operation, the bit 132 may be a drill type bit having rotating teeth that can cut through the formation 102 to create the wellbore 120. During a coring operation, the bit 132 may be a coring type bit that is operable to cut and extract samples of formation rock (or "core samples" or "cores") 142 from the formation 102. The core sample 142 may be, for example, a solid cylindrical continuous section of rock of the formation 102, often referred to as a "conventional core" or a "whole core." In such an embodiment, the coring type bit 132 may be a hollow cylindrical bit that is lowered into engagement with rock of the formation 102 at a down-hole end of the wellbore 120 and that is rotated (for example, by way of rotation of the drill pipe of a drill string of the drilling system 130) to cut and retrieve the solid cylinder of the rock of the formation 102 from the wellbore 120.

In some embodiments, one or more of the core samples 142 extracted from the well 106 (or other wells) are transported to the core laboratory 110 for laboratory assessment. Laboratory assessment of a core sample 142 may include conducting tests on the core sample 142 in the laboratory environment to identify characteristics (or "properties") of the core sample 142. The characteristics may include, for example, density, porosity, permeability, fluid saturation, grain density, lithology or texture of the rock forming the core sample 142. In some embodiments, the characteristics identified are used to generate a core log 162 for the well 106. A core log 162 for the well 106 may include a record identifying characteristics of the wellbore 120 of the well 106 (for example, including characteristics of the rock of the formation 102 surrounding the wellbore 120) versus depth in the wellbore 120 that are determined based on core data 164 obtained by way of laboratory assessment of one or more core samples 142 extracted from the well 106. For example, multiple core samples 142 may be extracted across a depth interval of the formation 102 (e.g., a full depth interval of the formation 102 that extends across a depth interval of 100 meters (m) to 200 m within the wellbore 120), the extracted core samples 142 may be transported to the core laboratory 110 where they are subjected to laboratory tests to determine respective values of porosity for each of the core samples 142, and the respective values of porosity may be assembled and recorded in a core log 162 that maps the varying values of porosity across the depth interval (e.g., across the full depth interval of 100 m to 200 m).

In some embodiments, the core laboratory 110 includes a laboratory facility that physically houses one or more core samples 142 for assessment. For example, core samples 142 extracted from the well 106 (or other wells) may be transported to the core laboratory 110 where they are stored and provided for on-site (or remote) inspection and testing. In some embodiments, the core laboratory 110 includes a robotic core inspection system 150 that is operable to conduct geological core visualization, examination and digitization. In some embodiments, the robotic core inspection system 150 includes a robotic positioning system 152, a core sample sensing system 154, a core sample interaction system 156, and a control/communications system 158. In some embodiments, the control/communications system 158 includes a computer system that is the same as or similar to that of computer system 1000 described with regard to at least FIG. 4.

In some embodiments, the robotic positioning system 152 includes a robotic system that provides for physically supporting and positioning the core sample sensing system 154 and the core sample interaction system 156 relative to the core samples 142 physically present in the core laboratory 110. The robotic positioning system 152 may include, for example, a Cartesian robotic system (e.g., a robotic system capable of making linear movement in X, Y and Z directions) suspended above a core examination table or other supporting surface on which core samples 142 are disposed for inspection (e.g., suspended from a ceiling above a core examination table on which core samples 142 are disposed for inspection) in the core laboratory 110.

In some embodiments, the core sample sensing system 154 includes sensors for inspecting the core samples 142 in the core laboratory 110. The core sample sensing system 154 may include, for example, an optical image sensor (e.g., a high-resolution camera system), an ultraviolet (UV) imaging sensor (e.g., a UV camera), ultrasonic sensors, hyperspectral sensors, or position sensors (e.g., position sensors for determining relative positions of the sensors and other elements of the inspection system to the core samples 142). The core sample sensing system 154 may, for example, be capable of conducting image processing, such as pattern and text recognition, for identifying and associating visual elements (e.g., barcode or visible features of the rock of the core samples 142) with particular ones, or portions of, the core samples 142.

In some embodiments, the core sample interaction system 156 includes devices for physically interacting with the core samples 142 in the core laboratory 110. The core sample interaction system 156 may include, for example, dispensers for dispensing substances onto the core samples 142 (e.g., water or chemical spray systems), or scoring devices for physically scoring the core samples 142 (e.g., scoring (or "etching") systems for exposing the rock features of the core samples 142 (e.g., by way of "scratching" the core samples 142).

In some embodiments, the control/communications system 158 controls operation of the robotic core inspection system 150, including operational control, data processing and data communication. In some embodiments, the control/communications system 158 provide for remote controlled operation of the robotic core inspection system 150. For example, the control/communications system 158 may enable persons at remote locations to control operation of the robotic geologic core inspection system, such as loading, scanning, sensing and interaction operations described here. In some embodiments, the control/communications system 158 provides for the exchange of data. For example, the control/communications system 158 may enable core data 164 (for example, photographic images captures at the core laboratory 110 by the robotic core inspection system 150) to be communicated between the robotic core inspection system 150 and the one more remote geological core inspection systems 112 for viewing by personnel at the respective locations. In some embodiments, the control/communications system 158 provides for communication between personnel at the core laboratory 110 and the one more remote geological core inspection systems 112. For example, the control/communications system 158 may enable the exchange of audio and video between personnel at the core laboratory 110 and the one or more remote geological core inspection systems 112. Such a geological core inspection system 108 may reduce or eliminate the need for persons to be physically present at the core laboratory 110 to inspect the core samples 142. This may help to reduce or eliminate physical overcrowding in the core laboratory 110, or may reduce or eliminate the time and costs associated with persons having to travel to and from the core laboratory 110, which can help improve the efficiency and quality of core sample assessments.

In some embodiments, the network 114 includes an element or system that facilitates communication between the control/communications system 158 of the robotic core inspection system 150 and the one more remote geological core inspection systems 112. For example, the network 114 may include an electronic communications network, such as a local area network (LAN), a wide area network (WAN), a wireless local area network (WLAN), a cellular communications network, a short range wireless communications network (e.g., a Bluetooth wireless network), the Internet, or an industrial network. In some embodiments, the network 114 includes a single network or a combination of networks. In some embodiments, a remote inspection system includes a computer system that is the same as or similar to that of computer system 1000 described with regard to at least FIG. 4.

Figure 2:
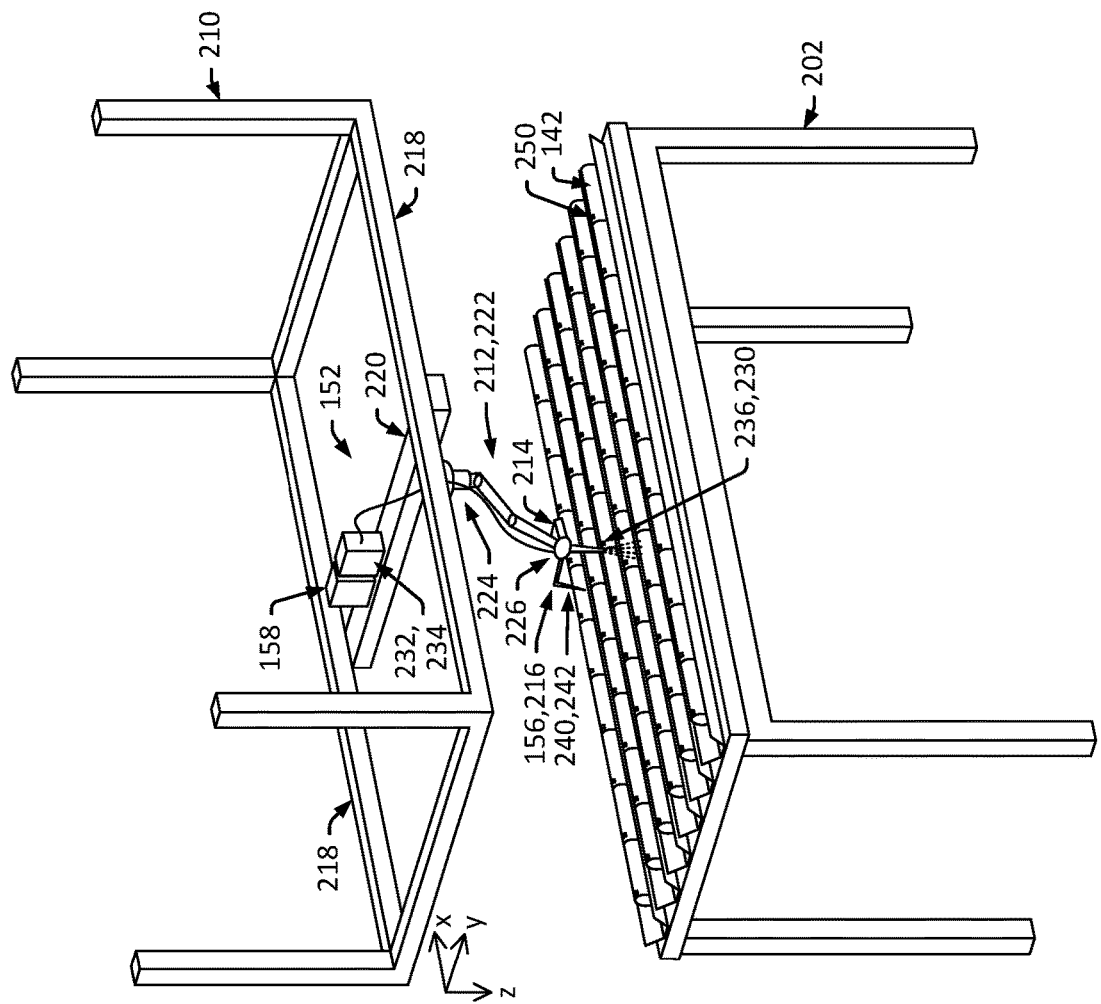
FIG. 2 is diagram that illustrates a geological core inspection system in accordance with one or more embodiments.

FIG. 2 is a diagram that illustrates an example core laboratory 110 including a robotic core inspection system 150 in accordance with one or more embodiments. The robotic core inspection system 150 may provide for on-site or remote inspection of core samples 142 disposed on a core examination table 202 located in the core laboratory 110. In the illustrated embodiment, the robotic core inspection system 150 includes a robotic positioning system 152, a core sample sensing system 154, a core sample interaction system 156, and a control/communications system 158.

In some embodiments, the robotic positioning system 152 provides for positioning of inspection devices of the core sample sensing system 154 and the core sample interaction system 156 relative to the core samples 142 and the core examination table 202. For example, the robotic positioning system 152 may include a Cartesian robotic system that includes a frame 210 and a robotic arm assembly 212 that is operable to move sensors 214 of the core sample sensing system 154 and interactive devices 216 of the core sample interaction system 156 in X, Y and Z directions relative to the core samples 142 and the core examination table 202. The frame 210 may be, for example, a rigid fame suspended from a ceiling of core laboratory 110 and having longitudinal rails 218. The robotic arm assembly 212 may include, for example, a robotic base 220 and robotic arm 222. The robotic base 220 may support the robotic arm 222. The robotic arm 222 may be an articulated robotic arm having a proximal end 224 secured to the robotic base 220 and a distal end 226 that supports the sensors 214 and interactive devices 216. The robotic base 220 may be operable to travel in the X direction along the longitudinal rails 218 of the frame 210 to move the robotic arm 222 (and the sensors 214 and the interactive devices 216) in the X direction relative to the core samples 142 and the core examination table 202. The robotic arm assembly 212 may be operable to move the distal end 226 of the robotic arm 222 (and the sensors 214 and the interactive devices 216) in the X, Y and Z directions relative to the robotic base 220. During use, the robotic positioning system 152 may be controlled to position the sensors 214 of the core sample sensing system 154 or the interactive devices 216 of the core sample interaction system 156 for inspection of one or more of the core samples 142. For example, the robotic positioning system 152 may be controlled such that the sensors 214 of the core sample sensing system 154 are located sufficiently close to a core sample 142 for sensing characteristics of the core sample 142 or such that the interactive devices 216 of the core sample interaction system 156 are located sufficiently close to a core sample 142 to enable physically interaction with the core sample 142.

In some embodiments, the sensors 214 of the core sample sensing system 154 includes an optical image sensor. For example, the sensors 214 may include a high-resolution camera that is operable to acquire high-resolution images of the core samples 142. In some embodiments, the sensors 214 of the core sample sensing system 154 include an ultraviolet (UV) imaging sensor. For example, the sensors 214 may include a UV camera that is operable to acquire UV images of the core samples 142. In some embodiments, the sensors 214 of the core sample sensing system 154 include an ultrasonic sensor. For example, the sensors 214 may include an ultrasound camera that is operable to acquire ultrasonic images of the core samples 142. In some embodiments, the sensors 214 of the core sample sensing system 154 include a hyperspectral sensor. For example, the sensors 214 may include a hyperspectral camera that is operable to acquire hyperspectral images of the core samples 142 that are indicative of electromagnetic characteristics of the core samples 142. In some embodiments, the sensors 214 of the core sample sensing system 154 include a magnetic sensor. For example, the sensors 214 may include a magnetic susceptibility sensor that is operable to sense magnetization of the core samples 142. In some embodiments, the sensors 214 of the core sample sensing system 154 include an X-Ray sensor. For example, the sensors 214 may include an X-Ray fluorescence (XRF) sensor that is operable to sense elemental of chemical characteristics of the core samples 142. In some embodiments, the sensors 214 of the core sample sensing system 154 include a color sensor. For example, the sensors 214 may include a color spectrometer sensor that is operable to sense color characteristics of the core samples 142. In some embodiments, the sensors 214 of the core sample sensing system 154 include a profile sensor. For example, the sensors 214 may include a three-dimensional (3D) laser profile sensor that is operable to sense physical profiles of the core samples 142. The physical profiles of the core samples 142 may be used, for example, to identify a mapping of physical characteristics of the surface of the core samples 142, or a core sample mapping 166 that maps the positioning (or "layout") of the core samples 142 on the core examination table 202. In some embodiments, the sensors 214 of the core sample sensing system 154 include a position sensor. For example, the sensors 214 may include an infrared proximity sensor that is operable to determine a distance of the sensor (or other elements of the arm assembly 212) from the core samples 142. The distance may be used, for example, to determine a position of the distal end 226 of the arm 222, the sensors 214, or the interactive devices 216, relative to a core sample 142. In some embodiments, the sensors 214 of the core sample sensing system 154 include a bar code sensor. For example, the sensors 214 may include a bar code scanner that is operable to read bar code type core identifiers 250 associated with the core samples 142.

In some embodiments, the interactive devices 216 of the core sample interaction system 156 include a dispenser system. For example, the interactive devices 216 may include a spray system 230 that is operable to dispense substances, such as water or chemicals, onto the core samples 142. Referring to FIG. 2, the spray system may include, for example, a fluid reservoir 232, a pump 234, and a nozzle 236 secured to the distal end 226 of the arm 222. During use, the distal end 226 of the arm 222 and the nozzle 236 may be moved into positon proximate a core sample 142, and the pump 234 may be operated to draw fluid from the reservoir 232 and force the fluid through the nozzle 236 to spray the fluid onto a surface of the core sample 142.

In some embodiments, the interactive devices 216 of the core sample interaction system 156 include a scoring system. For example, the interactive devices 216 may include a scoring system 240 that is operable to physically score (or "scratch" or "etch") the surface of the core samples 142. Referring to FIG. 2, the scoring system 240 may include, for example, a scoring arm 242 that extends from the distal end 226 of the arm 222. During use, the distal end 226 of the arm 222 and the scoring arm 242 may be moved into positon proximate a core sample 142, the scoring arm 242 may be extended, and the positioning of the arm 222 (or the positioning of the scoring arm 242) may be controlled to cause a distal end of the scoring arm 242 to score the surface of the core sample 142.

In some embodiments, one or more core samples 142 are loaded onto the core examination table 202 located in the core laboratory 110. For example, an array of core samples 142 may be positioned onto the core examination table 202 located in the core laboratory 110. The array of core samples 142 may include multiple rows of core samples 142 extending across a length of the core examination table 202. In some embodiments, the core samples 142 may be manually loaded onto the core examination table 202. For example, laboratory personal present in the core laboratory 110 may retrieve core samples 142 from storage and arrange them on the core examination table 202. In some embodiments, the core samples 142 are automatically loaded onto the core examination table 202. For example, a core retrieval system may include a robotic system that retrieves core samples 142 from storage and arranges them on the core examination table 202. Such a core retrieval system may include a robotic system that includes a "retrieval" pick-and-place robotic system that retrieves core samples 142 from storage and places them on a conveyor belt that moves the core samples 142 from storage to the core examination table 202, and a "placement" pick-and-place robotic system that retrieves core samples 142 from the conveyor belt and places them on the core examination table 202. The "placement" pick-and-place robotic system may include, for example, the robotic positioning system 152.

In some embodiments, each of the core samples 142 is accompanied by a respective core identifier 250 located proximate the core sample 142. For example, each of the core samples 142 may be provided with a respective barcode that uniquely identifies the core sample 142 from the other core samples 142. In some embodiments, the core identifier 250 of a core sample 142 is associated with characteristics of the core sample 142. For example, a barcode for a core sample 142 may be associated with characteristics of the core sample 142 stored in the core data 164. The characteristics for a core sample 142 may include, for example, a well from which the core sample 142 was extracted, a depth interval from which the core sample 142 was extracted, a date the core sample 142 was extracted, and properties determined for the core sample 142, such as density, porosity, permeability, wettability, organic matter content, fluid content, or the like for the core sample 142.

In some embodiments, the robotic core inspection system 150 provides for automated inspection of the core samples 142. For example, the robotic core inspection system 150 may be operable to load the core samples 142, to conduct a scan of the core samples 142, and to conduct assessment of the core samples 142, including sensing characteristics of the core samples 142 and physically interacting with the core samples 142. Such a system may facilitate efficient and accurate assessment of the core samples 142.

In some embodiments, loading the core samples 142 includes positioning an array of core samples 142 onto the core examination table 202 located in the core laboratory 110. For example, the robotic core inspection system 150 may place the core samples 142 into an array of core samples 142 that includes multiple rows of core samples extending across a length of the core examination table 202.

In some embodiments, conducting a scan of the core samples 142 includes scanning the array of core samples 142 to determine their respective positions on the core examination table 202. For example, the robotic positioning system 152 may be moved above the core examination table 202 while a camera of the core sample sensing system 154 captures a photographic image of the core samples 142 (and their core identifiers 250) from above and a profile sensor captures a physical profile of the core samples 142 from above. The physical profile of the core samples 142 may be assessed to identify the location and physical extents (e.g., left side, right side, top end, and bottom end) of each of the core samples 142, and the photographic image may be assessed to determine an identifier associated with each of the respective core samples 142. The location information and respective core identifiers 250 may be used to generate a core array mapping 166 that associates each of the core identifiers 250 with the location and extents of the corresponding core samples 142. For example, if a core sample 142 having a core identifier 250 of A12DF is located in an rectangular area defined by a left side at Y=0.45 m, a right side at Y=0.55 m, a top end at X=1.1 m and a bottom end at X=0.9 m, the mapping 166 may include an entry having A12DF associated with a location of (X=1.0 m, Y=0.5 m, Z=0.1 m) and extents of ($Y_{LS}$=0.45 m, $Y_{RS}$=0.55 m, $X_{TE}$=1.1 m, $X_{BE}$=0.9 m, Z=0.1 m). The mapping 166 may include a similar entry for each of the core samples 142 on the core examination table 202.

In some embodiments, sensing characteristics of the core samples 142 includes employing a sensor 214 of the core sample sensing system 154 to sense a corresponding characteristic of a core sample 142. For example, if the core sample 142 having the core identifier 250 of A12DF is to be subject to ultrasonic assessment, the location of (X=1.0 m, Y=0.5 m, Z=0.1 m) and the extents of ($Y_{LS}$=0.45 m, $Y_{RS}$=0.55 m, $X_{TE}$=1.1 m, $X_{BE}$=0.9 m) may be identified based on corresponding data of the core array mapping 166, the robotic arm assembly 212 of the robotic positioning system 152 may be moved and articulated to place the ultrasonic sensor of the sensors 214 proximate the location of (X=1.0 m, Y=0.5 m, Z=0.05 m) (which is just above the "top" surface of the core sample 142), and the robotic arm assembly 212 may be moved and articulated to move the ultrasonic sensor of the sensors 214 above the extents of the core sample 142 while the ultrasonic sensor acquires ultrasonic measurements of the top surface of the core sample 142 to generate an ultrasonic mapping of the top surface of the core sample 142. The others of the sensors 214 may be positioned and operated in a similar manner to acquire corresponding measurements of the core sample 142 which can be used to characterize the core sample 142. In some embodiments, multiple measurements may be acquired simultaneously. For example, a high resolution camera may be operated during the "scan" of the ultrasonic senor to acquire a high resolution image of the core sample 142 and the ultrasonic mapping of the core sample 142 simultaneously. This may improve the speed and efficiency of the assessment of the core sample 142.

In some embodiments, physically interacting with the core samples 142 includes employing an interactive device 216 of the core sample interaction system 156 to physically engage a core sample 142. For example, if the core sample 142 having the core identifier 250 of A12DF is to be subject to a chemical spray (or scoring), the location of (X=1.0 m, Y=0.5 m, Z=0.1 m) and the extents of ($Y_{LS}$=0.45 m, $Y_{RS}$=0.55 m, $X_{TE}$=1.1 m, $X_{BE}$=0.9 m) may be identified based on the core array mapping 166, the robotic arm assembly 212 of the robotic positioning system 152 may be moved and articulated to place the nozzle 236 (or scoring arm 242) of the core sample interaction system 156 proximate the location of (X=1.0 m, Y=0.5 m, Z=0.05 m) (which is just above the "top" surface of the core sample 142), and the pump 234 may be activated to spray the chemical onto the top surface of the core sample 142 (or the scoring arm 242 may be articulated to score the top surface of the core sample 142). In some embodiments, the sensors 214 may be operated to monitor the physical interaction or the results thereof. For example, a camera may be operated to acquire video of the spraying (or scoring) of the core sample 142 or video of the core sample 142 after the spraying (or scoring).

In some embodiments, the data sensed by the core sample sensing system 154, or a record of the physical interactions of the core sample interaction system 156, is recorded in the core data 164. Continuing with the prior example, the core data 164 may include the high resolution image of the core sample 142, the ultrasonic mapping of the core sample 142, a record of the spray of the chemical (e.g., including the time and date of the spraying, the type of chemical sprayed, the volume of the chemical sprayed on to the core sample 142, and the video of the spraying of the core sample 142) and a record of the scoring of the top surface of the core sample 142 (e.g., including the time and date of the scoring, the location of the scoring on the surface of the core sample 142, and the video of the scoring of the core sample 142). As a further example, the core array mapping 166 (which defines location of core samples 142 that are presented for assessment in the core laboratory 110) may be stored in the core data 164.

In some embodiments, the control/communications system 158 facilitates remote control of the robotic core inspection system 150 by the one or more remote geological core inspection systems 112. For example, the control/communications system 158 may control operations of the robotic core inspection system 150 to perform loading, scanning, sensing and interaction operations described here. In some embodiments, a person at a remote geological core inspection system 112 may interact with a computer terminal of the remote geological core inspection system 112 to issue operational commands for the robotic core inspection system 150, the remote geological core inspection system 112 may communicate the operational commands to the control/communications system 158 of the robotic core inspection system 150 by way of the network 114, and the control/communications system 158 may control operation of the robotic core inspection system 150 to carry out corresponding operations. For example, a geologist physically present at the remote geological core inspection system 112 may interact with a computer terminal of the remote geological core inspection system 112 to issue an operational command that requests a photographic image of the core sample 142 having the core identifier 250 of A12DF, the remote geological core inspection system 112 may communicate a corresponding operational command to the control/communications system 158 by way of the network 114, and the control/communications system 158 may control the robotic core inspection system 150 to position a camera sensor above the core sample 142 and acquire a photographic image of the core sample 142 and store the photographic image in the core data 164 in association with the core identifier 250 of A12DF.

In some embodiments, the control/communications system 158 facilitates exchange of data between the robotic core inspection system 150 and the one or more remote geological core inspection systems 112. For example, the remote geological core inspection system 112 may broadcast some or all of the core data 164 to one or more of the remote geological core inspection systems 112 for display and viewing. For example, in response to the operational command that requests a photographic image of the core sample 142 having the core identifier 250 of A12DF and the acquisition of the photographic image, the control/communications system 158 may communicate the photographic image to the remote geological core inspection system 112 by way of the network 114, and the remote geological core inspection system 112 may display the photographic image at a graphical user interface of the terminal for viewing by the geologist.

In some embodiments, the control/communications system 158 includes a "local" computer terminal (for example, a computer terminal located in the core laboratory 110) that facilitates "local" control of the robotic core inspection system 150 and local interaction with the core data 164. For example, a geologist physically present in the core laboratory 110 may issue control commands and view core data 164 by way of the local computer terminal. In some embodiments, the local and remote terminals provide for communication between persons physically present at the core laboratory and persons located at the remote locations of the remote geological core inspection system 112.

In some embodiments, the core data 164 is used to assess the core samples 142 and the formation 102. For example, the characteristics of the core data 164 for core samples 142 extracted from different depths of the wellbore 120 of the well 106 may be assembled generate a core log 162 for the well 106. If, for example, the core data 164 includes porosity of the core samples 142 extracted from across the depth interval of 100 m-200 m within the wellbore 120 of the well 106 determined based on the assessment in the core laboratory 110, the porosity values may be assembled to generate a porosity type core log 162 that indicates porosity of the formation 102 across the depth interval of 100 m-200 m.

In some embodiments, the formation 102 is developed based the assessment of the core samples 142 and the associated core data 164. This may include defining or conducting various operations for development of the formation 102 based on the core data 164. For example, the well control system 122 (or another operator of the formation 102) may determine, based on the core log 162, drilling parameters (e.g., well locations and trajectories) or operating parameters (e.g., production rates and pressures or injection rates and pressure) for the well 106 (or other wells in the formation 102), or may control drilling or operation of the well 106 (or other wells in the formation 102) in accordance with the drilling or operating parameters (e.g., to drill a well at a determined location or having a determined trajectory, or to operate a well at a determined rate or pressure). In some embodiments, development of the formation 102 includes generating a model of a reservoir in the formation 102 (or a "reservoir model"). For example, the well control system 122 (or another operator of the formation 102) may determine, based the assessment of the core samples 142 and the associated core data 164, a three-dimensional model of the formation 102. The model may be used, for example, to assess the current state of the formation 102, to predict a future state of the formation 102, or to determine actions to be taken to develop the formation 102. In some embodiments, the drilling or operating parameters for the well 106 (or other wells in the formation 102) may be determined based on the reservoir model.

Figure 3:
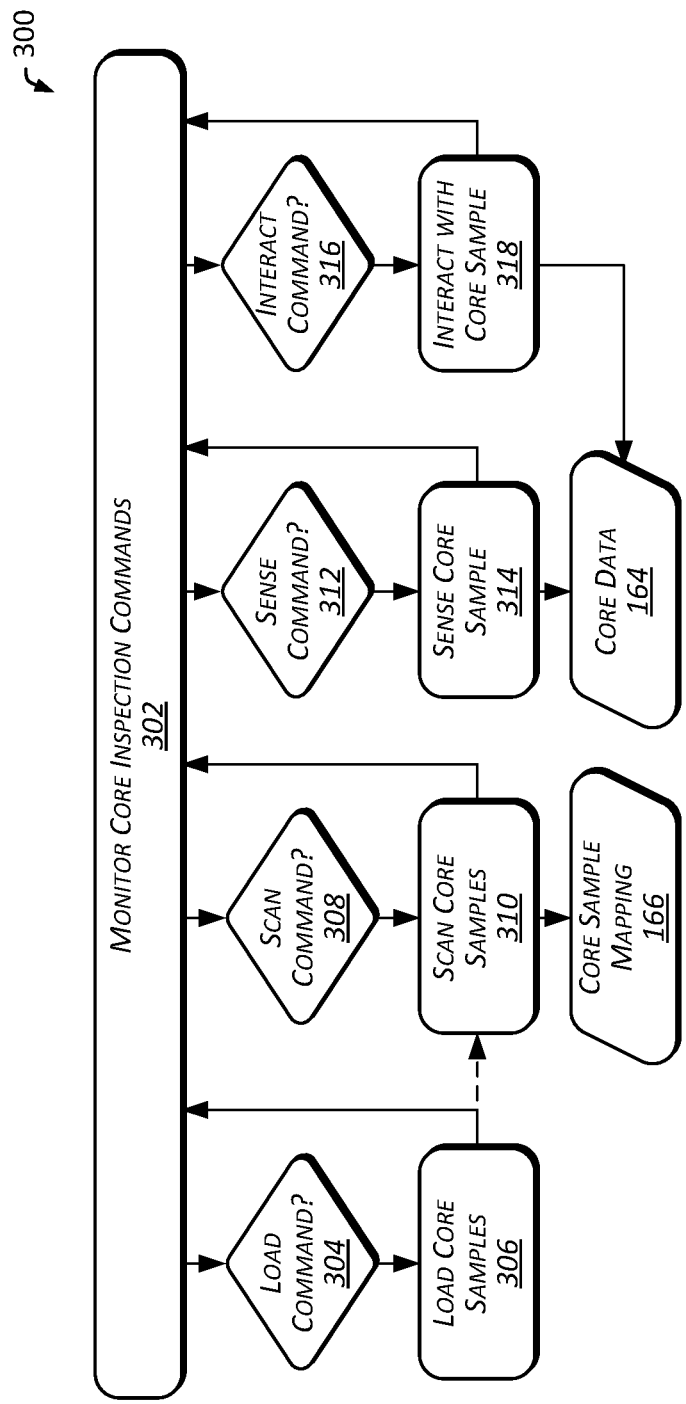
FIG. 3 is a flowchart that illustrates a method of geological core inspection in accordance with one or more embodiments.

FIG. 3 is a flowchart that illustrates a method 300 of conducting a geological core inspection in accordance with one or more embodiments. Method 300 may include monitoring core inspection commands (block 302). In some embodiments, monitoring core inspection commands includes monitoring for core inspection commands received by way of a "local" computer terminal of the robotic core inspection system 150 or a "remote" computer terminal of a remote geological core inspection system 112. For example, monitoring core inspection commands may include the control/communications system 158 of the robotic core inspection system 150 monitoring for core inspection commands received by way of a "local" computer terminal of the robotic core inspection system 150 located in the core laboratory 110 or a "remote" computer terminal of a remote geological core inspection system 112 that is located in a facility that is remote from the core laboratory 110 (e.g., located in another room or in another building). Continuing with the prior examples, the core inspection command may include a command to conduct a loading, a scanning, a sensing or an interaction operation, such as those described here. For example, a geologist physically present at the remote geological core inspection system 112 may interact with a "remote" computer terminal of the remote geological core inspection system 112 to issue an operational command that requests a photographic image of the core sample 142 having the core identifier 250 of A12DF, the remote geological core inspection system 112 may communicate a corresponding operational command to the control/communications system 158 by way of the network 114, and the control/communications system 158 may receive the corresponding operational command during its monitoring for core inspection commands.

Method 300 may include, in response to receiving a core inspection command, executing a corresponding core inspection operation. In some embodiments, in response to receiving a load command (block 304), a load core samples operation is conducted (block 306). A load core samples operation may include positioning an array of core samples 142 in the core laboratory 110 for inspection. For example, a load core samples operation may include the control/communications system 158 controlling the robotic core inspection system 150 to place core samples 142 into an array of core samples 142 that includes multiple rows of core samples extending across a length of the core examination table 202 in the core laboratory 110, for inspection.

In some embodiments, in response to receiving a scan command (block 308), a scan core samples operation is conducted (block 310). A scan core samples operation may include scanning an array of core samples 142 positioned in the core laboratory 110 for inspection to determine their respective positions. For example, a scan core samples operation may include the control/communications system 158 controlling the robotic core inspection system 150 to move the robotic positioning system 152 above the core examination table 202 while a camera of the core sample sensing system 154 captures a photographic image of the core samples 142 (and their core identifiers 250) from above and a profile sensor captures a physical profile of the core samples 142 from above. The scan core samples operation may include the control/communications system 158 assessing the physical profile of the core samples 142 to identify the location and physical extents (e.g., left side, right side, top end, and bottom end) of each of the core samples 142, assessing the photographic image to determine an identifier associated with each of the respective core samples 142, and generating a core array mapping 166 that associates each of the core identifiers 250 with the location and extents of the corresponding core samples 142. For example, if the core sample 142 having the core identifier 250 of A12DF is located in an rectangular area defined by a left side at Y=0.45 m, a right side at Y=0.55 m, a top end at X=1.1 m and a bottom end at X=0.9 m, the mapping 166 may include an entry having A12DF associated with the location of (X=1.0 m, Y=0.5 m, Z=0.1 m) and the extents of ($Y_{LS}$=0.45 m, $Y_{RS}$=0.55 m, $X_{TE}$=1.1 m, $X_{BE}$=0.9 m, Z=0.1 m). The mapping 166 may include a similar entry for each of the core samples 142 on the core examination table 202.

In some embodiments, in response to receiving a sense command (block 312), a sense core sample operation is conducted (block 314). A sense core sample operation may include employing a sensor 214 of the core sample sensing system 154 to sense a corresponding characteristic of a core sample 142. For example, if a sense command requests that the core sample 142 having the core identifier 250 of A12DF is to be subject to ultrasonic assessment, the control/communications system 158 may identify the location of (X=1.0 m, Y=0.5 m, Z=0.1 m) and the extents of ($Y_{LS}$=0.45 m, $Y_{RS}$=0.55 m, $X_{TE}$=1.1 m, $X_{BE}$=0.9 m) based on corresponding data of the core array mapping 166, the control/communications system 158 may control the robotic arm assembly 212 of the robotic positioning system 152 to place the ultrasonic sensor of the sensors 214 proximate the location of (X=1.0 m, Y=0.5 m, Z=0.05 m) (which is just above the "top" surface of the core sample 142), the control/communications system 158 may control the robotic arm assembly 212 to move the ultrasonic sensor of the sensors 214 above the extents of the core sample 142 while the ultrasonic sensor acquires ultrasonic measurements of the top surface of the core sample 142 to generate an ultrasonic mapping of the top surface of the core sample 142, and the control/communications system 158 may store the ultrasonic mapping in the core data 164.

In some embodiments, in response to receiving an interact command (block 316), an interact with core sample operation is conducted (block 318). An interact with a core sample operation may include employing an interactive device 216 of the core sample interaction system 156 to physically engage a core sample 142. For example, if an interact command request that the core sample 142 having the core identifier 250 of A12DF is to be subjected to a chemical spray (or scoring), the control/communications system 158 may identify the location of (X=1.0 m, Y=0.5 m, Z=0.1 m) and the extents of ($Y_{LS}$=0.45 m, $Y_{RS}$=0.55 m, $X_{TE}$=1.1 m, $X_{BE}$=0.9 m) based on the core array mapping 166, the control/communications system 158 may control the robotic arm assembly 212 of the robotic positioning system 152 to place the nozzle 236 (or the scoring arm 242) of the core sample interaction system 156 proximate the location of (X=1.0 m, Y=0.5 m, Z=0.05 m) (which is just above the "top" surface of the core sample 142), and the control/communications system 158 may control the pump 234 to spray the chemical onto the top surface of the core sample 142 (or control the scoring arm 242 to score the top surface of the core sample 142). In some embodiments, an interact core sample operation may include operating the sensors 214 to monitor the physical interaction or results thereof. For example, the control/communications system 158 may control a camera of the sensors 214 to acquire images or video of the spraying (or scoring) operation or images or video of the core sample after the spraying (or scoring) to capture the effects of the spraying (or scoring). In some embodiments, the data sensed by the core sample sensing system 154 or a record of the physical interactions of the core sample interaction system 156 is recorded in the core data 164. Continuing with the above example, the control/communications system 158 may store the high resolution image of the core sample 142, the ultrasonic mapping of the core sample 142, a record of the spray of the chemical (e.g., including the time and date of the spraying, the type of chemical sprayed, the volume of the chemical sprayed on to the core sample 142, and the video of the spraying of the core sample 142) and a record of the scoring of the top surface of the core sample 142 (e.g., including the time and date of the scoring, the location of the scoring on the surface of the core sample 142, and the video of the scoring of the core sample 142) in the core data 164.

Figure 4:
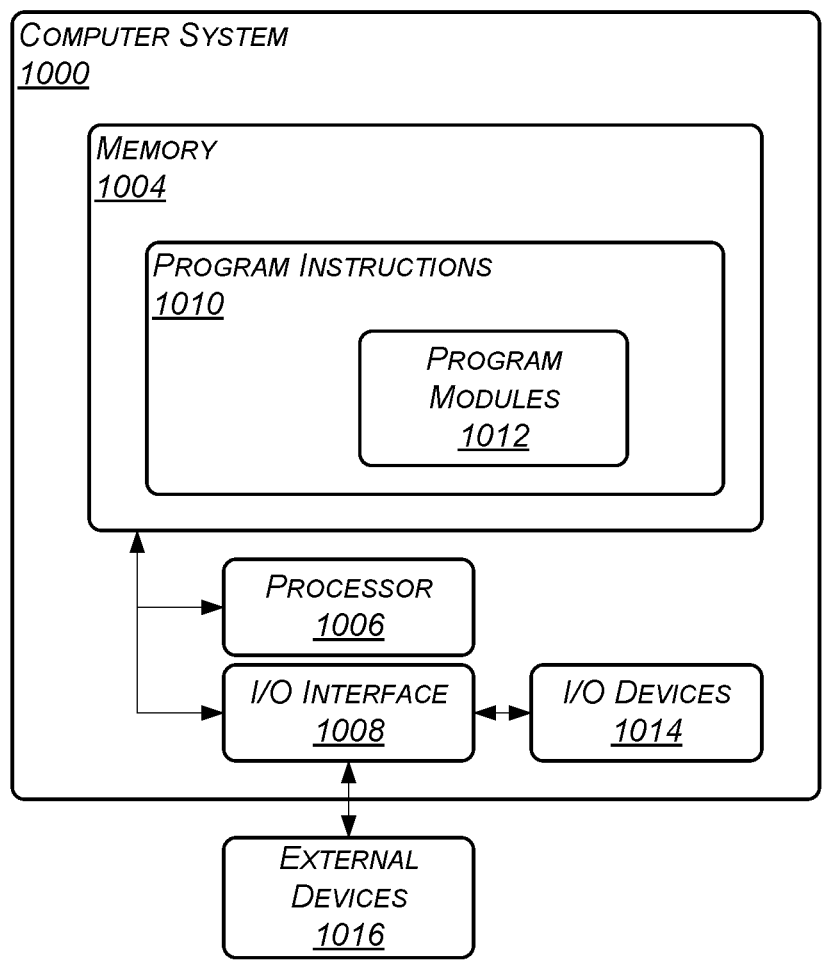
FIG. 4 is a diagram that illustrates an example computer system in accordance with one or more embodiments.

FIG. 4 is a diagram that illustrates an example computer system (or "system") 1000 in accordance with one or more embodiments. In some embodiments, the system 1000 is a programmable logic controller (PLC). The system 1000 may include a memory 1004, a processor 1006 and an input/output (I/O) interface 1008. The memory 1004 may include non-volatile memory (e.g., flash memory, read-only memory (ROM), programmable read-only memory (PROM), erasable programmable read-only memory (EPROM), electrically erasable programmable read-only memory (EEPROM)), volatile memory (for example, random access memory (RAM), static random access memory (SRAM), synchronous dynamic RAM (SDRAM)), or bulk storage memory (e.g., CD-ROM or DVD-ROM, hard drives). The memory 1004 may include a non-transitory computer-readable storage medium having program instructions 1010 stored thereon. The program instructions 1010 may include program modules 1012 that are executable by a computer processor (e.g., the processor 1006) to cause the functional operations described, such as those described with regard to the well control system 122 (or another operator of the well 106), the robotic core inspection system 150, the one more remote geological core inspection systems 112, or the method 300.

The processor 1006 may be any suitable processor capable of executing program instructions. The processor 1006 may include a central processing unit (CPU) that carries out program instructions (e.g., the program instructions of the program modules 1012) to perform the arithmetical, logical, or input/output operations described. The processor 1006 may include one or more processors. The I/O interface 1008 may provide an interface for communication with one or more I/O devices 1014, such as a joystick, a computer mouse, a keyboard, or a display screen (e.g., an electronic display for displaying a graphical user interface (GUI)). The I/O devices 1014 may include one or more of the user input devices. The I/O devices 1014 may be connected to the I/O interface 1008 by way of a wired connection (e.g., an Industrial Ethernet connection) or a wireless connection (e.g., a Wi-Fi connection). The I/O interface 1008 may provide an interface for communication with one or more external devices 1016. In some embodiments, the I/O interface 1008 includes one or both of an antenna and a transceiver. In some embodiments, the external devices 1016 include the well control system 122, the robotic core inspection system 150 or the remote geological core inspection systems 112.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments. It is to be understood that the forms of the embodiments shown and described here are to be taken as examples of embodiments. Elements and materials may be substituted for those illustrated and described here, parts and processes may be reversed or omitted, and certain features of the embodiments may be utilized independently, all as would be apparent to one skilled in the art after having the benefit of this description of the embodiments. Changes may be made in the elements described here without departing from the spirit and scope of the embodiments as described in the following claims. Headings used here are for organizational purposes only and are not meant to be used to limit the scope of the description.

It will be appreciated that the processes and methods described here are example embodiments of processes and methods that may be employed in accordance with the techniques described here. The processes and methods may be modified to facilitate variations of their implementation and use. The order of the processes and methods and the operations provided may be changed, and various elements may be added, reordered, combined, omitted, modified, and so forth. Portions of the processes and methods may be implemented in software, hardware, or a combination of software and hardware. Some or all of the portions of the processes and methods may be implemented by one or more of the processors/modules/applications described here.

As used throughout this application, the word "may" is used in a permissive sense (that is, meaning having the potential to), rather than the mandatory sense (that is, meaning must). The words "include," "including," and "includes" mean including, but not limited to. As used throughout this application, the singular forms "a", "an," and "the" include plural referents unless the content clearly indicates otherwise. Thus, for example, reference to "an element" may include a combination of two or more elements. As used throughout this application, the term "or" is used in an inclusive sense, unless indicated otherwise. That is, a description of an element including A or B may refer to the element including one or both of A and B. As used throughout this application, the phrase "based on" does not limit the associated operation to being solely based on a particular item. Thus, for example, processing "based on" data A may include processing based at least in part on data A and based at least in part on data B, unless the content clearly indicates otherwise. As used throughout this application, the term "from" does not limit the associated operation to being directly from. Thus, for example, receiving an item "from" an entity may include receiving an item directly from the entity or indirectly from the entity (for example, by way of an intermediary entity). Unless specifically stated otherwise, as apparent from the discussion, it is appreciated that throughout this specification discussions utilizing terms such as "processing," "computing," "calculating," "determining," or the like refer to actions or processes of a specific apparatus, such as a special purpose computer or a similar special purpose electronic processing/computing device. In the context of this specification, a special purpose computer or a similar special purpose electronic processing/computing device is capable of manipulating or transforming signals, typically represented as physical, electronic or magnetic quantities within memories, registers, or other information storage devices, transmission devices, or display devices of the special purpose computer or similar special purpose electronic processing/computing device.

What is claimed is:

1. A method of remote geological core inspection, the method comprising:
    positioning, on a core sample inspection table, an array of core samples;
    conducting, by a robotic core inspection system, a scanning of the array of core samples to identify positions of the core samples of the array of core samples;
    generating, by the robotic core inspection system based on the positions of the core samples identified, a core sample mapping identifying locations of the core samples on the core sample inspection table;
    receiving, by the robotic core inspection system, a command to conduct an inspection operation for a given core sample of the core samples;
    determining, based on the core sample mapping, a location of the given core sample;
    positioning, by the robotic core inspection system, an inspection device proximate the location of the given core sample; and
    conducting, by the robotic core inspection system, the inspection operation for the given core sample, the inspection operation comprising:
        moving a scoring device proximate the location of the given core sample;
        operating the scoring system to score a surface of the given core sample; and
        acquiring an image of scoring of the surface of the core sample to capture the effects of the scoring thereby helping to improve efficiency and quality of core sample assessments.

2. The method of claim 1, wherein the scanning of the array of core samples comprises capturing a photographic image of the array of core samples.

3. The method of claim 1, wherein the scanning of the array of core samples comprises capturing a physical profile of the core samples.

4. The method of claim 1, wherein each core sample of the array of core samples comprises a corresponding core identifier, and wherein the core sample mapping associates each core sample of the array of core samples with the corresponding core identifier.

5. The method of claim 4, wherein the command to conduct an inspection operation for the given core sample identifies the core identifier corresponding to the given core sample, and wherein the location of the given core sample is determined based on a location of the core sample mapping that corresponds to the core identifier corresponding to the given core sample.

6. The method of claim 1, wherein the inspection operation comprises a sensing operation comprising moving a sensor proximate the location of the given core sample to sense a corresponding characteristic of the core sample.

7. The method of claim 1, wherein the inspection operation comprises an interactive operation comprising moving an interactive device proximate the location of the given core sample to physically interact with the core sample.

8. The method of claim 1, wherein the inspection operation comprises an interactive spraying operation comprising moving a spray device proximate the location of the given core sample and operating the spray system to spray a substance on a surface of the given core sample.

9. A non-transitory computer readable storage medium comprising program instructions stored thereon that are executable by a computer processor to perform a geological core inspection comprising the following operations:

conducting, by a robotic core inspection system, a scanning of an array of core samples positioned on a core sample inspection table in a geological core inspection laboratory to identify positions of the core samples of the array of core samples;

generating, by the robotic core inspection system based on the positions of the core samples identified, a core sample mapping identifying locations of the core samples on the core sample inspection table;

receiving, by the robotic core inspection system, a command to conduct an inspection operation for a given core sample of the core samples;

determining, by the robotic core inspection system based on the core sample mapping, a location of the given core sample;

positioning, by the robotic core inspection system, an inspection device proximate the location of the given core sample; and conducting, by the robotic core inspection system, the inspection operation for the given core sample, the inspection operation comprising:

moving a scoring device proximate the location of the given core sample;

operating the scoring system to score a surface of the given core sample; and acquiring an image of scoring of the surface of the core sample to capture the effects of the scoring thereby helping to improve efficiency and quality of core sample assessments.

10. A geological core inspection system comprising:

a robotic core inspection system comprising a control and communications system a robotic core inspection system comprising non-transitory computer readable storage medium comprising program instructions stored thereon that are executable by a computer processor to perform a geological core inspection comprising the following operations:

conducting a scanning of the array of core samples to identify positions of the core samples of the array of core samples;

generating, on the positions of the core samples identified, a core sample mapping identifying locations of the core samples on the core sample inspection table;

receiving a command to conduct an inspection operation for a given core sample of the core samples;

determining, based on the core sample mapping, a location of the given core sample;

positioning an inspection device proximate the location of the given core sample; and conducting the inspection operation for the given core sample, the inspection operation comprising:

moving a scoring device proximate the location of the given core sample;

operating the scoring system to score a surface of the given core sample; and acquiring an image of scoring of the surface of the core sample to capture the effects of the scoring thereby helping to improve efficiency and quality of core sample assessments.

\* \* \* \* \*